(12) United States Patent
Donelson et al.

(10) Patent No.: US 8,309,624 B2
(45) Date of Patent: Nov. 13, 2012

(54) HAZE REDUCTION FOR BLENDS OF AROMATIC-ALIPHATIC POLYESTERS AND ANTIMICROBIAL ADDITIVES

(75) Inventors: Michael Eugene Donelson, Kingsport, TN (US); James Collins Maine, Church Hill, TN (US); Gary Stuart Hawkins, Johson City, TN (US); Jeff Scott Howell, Jonesborough, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 13/097,701

(22) Filed: Apr. 29, 2011

(65) Prior Publication Data

US 2012/0184641 A1  Jul. 19, 2012

Related U.S. Application Data

(60) Provisional application No. 61/433,337, filed on Jan. 17, 2011.

(51) Int. Cl.
*C08K 3/10* (2006.01)
(52) U.S. Cl. ................................ 523/122; 524/403
(58) Field of Classification Search .................. 523/122; 524/403
See application file for complete search history.

(56) References Cited

U.S. PATENT DOCUMENTS

| | | |
|---|---|---|
| 5,372,864 A | 12/1994 | Weaver et al. |
| 5,384,377 A | 1/1995 | Weaver et al. |
| 5,480,926 A | 1/1996 | Fagerburg et al. |
| 5,654,347 A | 8/1997 | Khemani et al. |
| 5,696,176 A | 12/1997 | Khemani et al. |
| 5,783,307 A | 7/1998 | Fagerburg et al. |
| 6,352,783 B1 | 3/2002 | Fagerburg |
| 2006/0111481 A1 | 5/2006 | Pearson et al. |
| 2009/0123756 A1* | 5/2009 | Hashimoto et al. ............ 428/409 |

OTHER PUBLICATIONS

"Primary Antioxidants: Appendix A: Chemical Structures, CAS-Numbers, Producers and Tradenames of Stabilizers," Plastic Additives Handbook, $5^{th}$ Edition, 2001, pp. 98-108, Hanser Gardner Publications, Inc., Cincinnati, OH.
"Secondary Antioxidants/Phosphites/Phosphonites: Appendix A: Chemical Structures, CAS-Numbers, Producers and Tradenames of Stabilizers," Plastic Additives Handbook, 5th Edition, 2001, pp. 109-112, Hanser Gardner Publications, Inc., Cincinnati, OH.
Bergen, R. L., Jr., "Stress Cracking of Rigid Thermoplastics," SPE Journal, Technical Section, Jun. 1962, pp. 667-670.

\* cited by examiner

*Primary Examiner* — Kriellion Sanders
(74) *Attorney, Agent, or Firm* — Betty Joy Boshears

(57) ABSTRACT

This invention relates to a blend comprising:
(A) about 80% by weight to about 99.99% by weight of at least one polyester comprising terephthalic acid residues, 2,2,4,4-tetramethyl-1,3-cyclobutanediol residues; and 1,4-cyclohexanedimethanol residues; and
(B) about 0.01% by weight to about 20% by weight of at least one antimicrobial agent;
said weight percentages being based on the total weight of the blend.

38 Claims, No Drawings

HAZE REDUCTION FOR BLENDS OF AROMATIC-ALIPHATIC POLYESTERS AND ANTIMICROBIAL ADDITIVES

BACKGROUND OF THE INVENTION

The healthcare industry has a need for clarity in various medical device parts and medical packaging. Other industries benefit from clarity of blends as well. Part clarity improves the ability of the health care professional to observe fluid paths and to detect potential biofilm development. The healthcare industry also has a need to reduce hospital acquired infections by incorporating antimicrobial additives into various medical devices, packaging, housings, curtains and the like. Clarity in polymers with antimicrobial additives is difficult to achieve as the additives typically create haze when compounded into the polymer. Health care institutions often have had to sacrifice clarity to use parts with antimicrobial additives. Parts used in these applications typically range from translucent to opaque.

SUMMARY OF THE INVENTION

This invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 10 to 40 mole % of 2,2,4,4-tetramethyl-1,3-cyclobutanediol residues; and
    (ii) 60 to 90 mole % of 1,4-cyclohexanedimethanol residues,
  wherein the total mole % of the dicarboxylic acid component is 100 mole %, and the total mole % of the glycol component is 100 mole %; and
    about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 15 to 40 mole % of 2,2,4,4-tetramethyl-1,3-cyclobutanediol residues; and
    (ii) 60 to 85 mole % of 1,4-cyclohexanedimethanol residues,
  wherein the total mole % of the dicarboxylic acid component is 100 mole %, and the total mole % of the glycol component is 100 mole %; and
    about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 20 to 40 mole % of 2,2,4,4-tetramethyl-1,3-cyclobutanediol residues; and
    (ii) 60 to 80 mole % of 1,4-cyclohexanedimethanol residues,
  wherein the total mole % of the dicarboxylic acid component is 100 mole %, and the total mole % of the glycol component is 100 mole %; and
    about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 15 to 30 mole % of 2,2,4,4-tetramethyl-1,3-cyclobutanediol residues; and
    (ii) 70 to 85 mole % of 1,4-cyclohexanedimethanol residues,
  wherein the total mole % of the dicarboxylic acid component is 100 mole %, and the total mole % of the glycol component is 100 mole %; and
    about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and (b) a glycol component comprising:
(i) 20 to 30 mole % of 2,2,4,4-tetramethyl-1,3-cyclobutanediol residues; and
(ii) 70 to 80 mole % of 1,4-cyclohexanedimethanol residues, wherein the total mole % of the dicarboxylic acid component is 100 mole %, and the total mole % of the glycol component is 100 mole %; and about 0.01% by weight to about 20% by weight of at least one antimicrobial agent chosen from at least one of: silver oxides, silver zirconium phosphates, silver glass, silver silicas, or combinations thereof;

said weight percentages being based on the total weight of the blend.

In one aspect, the invention relates to a blend comprising about 80% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 30 to 40 mole % of 2,2,4,4-tetramethyl-1,3-cyclobutanediol residues; and
(ii) 60 to 70 mole % of 1,4-cyclohexanedimethanol residues, wherein the total mole % of the dicarboxylic acid component is 100 mole %, and the total mole % of the glycol component is 100 mole %; and about 0.01% by weight to about 20% by weight of at least one antimicrobial agent chosen from at least one of: silver oxides, silver zirconium phosphates, silver glass, silver silicas, or combinations thereof;

said weight percentages being based on the total weight of the blend.

In one aspect, the invention relates to a blend comprising about 95% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 10 to 40 mole % of 2,2,4,4-tetramethyl-1,3-cyclobutanediol residues; and
(ii) 60 to 90 mole % of 1,4-cyclohexanedimethanol residues, wherein the total mole % of the dicarboxylic acid component is 100 mole %, and the total mole % of the glycol component is 100 mole %; and about 0.01% by weight to about 5% by weight of at least one antimicrobial agent chosen from at least one of: silver oxides, silver zirconium phosphates, silver glass, silver silicas, or combinations thereof;

said weight percentages being based on the total weight of the blend.

In one aspect, the invention relates to a blend comprising about 95% by weight to about 99.99% by weight of at least one polyester comprising:

(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 15 to 40 mole % of 2,2,4,4-tetramethyl-1,3-cyclobutanediol residues; and
(ii) 60 to 85 mole % of 1,4-cyclohexanedimethanol residues, wherein the total mole % of the dicarboxylic acid component is 100 mole %, and the total mole % of the glycol component is 100 mole %; and about 0.01% by weight to about 5% by weight of at least one antimicrobial agent chosen from at least one of: silver oxides, silver zirconium phosphates, silver glass, silver silicas, or combinations thereof;

said weight percentages being based on the total weight of the blend.

In one aspect, the invention relates to a blend comprising about 95% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 20 to 40 mole % of 2,2,4,4-tetramethyl-1,3-cyclobutanediol residues; and
(ii) 60 to 80 mole % of 1,4-cyclohexanedimethanol residues, wherein the total mole % of the dicarboxylic acid component is 100 mole %, and the total mole % of the glycol component is 100 mole %; and about 0.01% by weight to about 5% by weight of at least one antimicrobial agent chosen from at least one of: silver oxides, silver zirconium phosphates, silver glass, silver silicas, or combinations thereof;

said weight percentages being based on the total weight of the blend.

In one aspect, the invention relates to a blend comprising about 95% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 15 to 30 mole % of 2,2,4,4-tetramethyl-1,3-cyclobutanediol residues; and
(ii) 70 to 85 mole % of 1,4-cyclohexanedimethanol residues, wherein the total mole % of the dicarboxylic acid component is 100 mole %, and the total mole % of the glycol component is 100 mole %; and about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 95% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 20 to 30 mole % of 2,2,4,4-tetramethyl-1,3-cyclobutanediol residues; and
(ii) 70 to 80 mole % of 1,4-cyclohexanedimethanol residues,
wherein the total mole % of the dicarboxylic acid component is 100 mole %, and the total mole % of the glycol component is 100 mole %; and
about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 95% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 30 to 40 mole % of 2,2,4,4-tetramethyl-1,3-cyclobutanediol residues; and
(ii) 60 to 70 mole % of 1,4-cyclohexanedimethanol residues,
wherein the total mole % of the dicarboxylic acid component is 100 mole %, and the total mole % of the glycol component is 100 mole %; and
about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 97% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 10 to 40 mole % of 2,2,4,4-tetramethyl-1,3-cyclobutanediol residues; and
(ii) 60 to 90 mole % of 1,4-cyclohexanedimethanol residues,
wherein the total mole % of the dicarboxylic acid component is 100 mole %, and the total mole % of the glycol component is 100 mole %; and
about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 97% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 15 to 40 mole % of 2,2,4,4-tetramethyl-1,3-cyclobutanediol residues; and
(ii) 60 to 85 mole % of 1,4-cyclohexanedimethanol residues,
wherein the total mole % of the dicarboxylic acid component is 100 mole %, and the total mole % of the glycol component is 100 mole %; and
about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 97% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 20 to 40 mole % of 2,2,4,4-tetramethyl-1,3-cyclobutanediol residues; and
(ii) 60 to 80 mole % of 1,4-cyclohexanedimethanol residues,
wherein the total mole % of the dicarboxylic acid component is 100 mole %, and the total mole % of the glycol component is 100 mole %; and
about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 97% by weight to about 99.99% by weight of at least one polyester comprising:

(a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and
  (iii) 0 to 30 mole % of residues of at least one modifying aliphatic dicarboxylic acid having up to 16 carbon atoms; and
(b) a glycol component comprising:
  (i) 15 to 30 mole % of 2,2,4,4-tetramethyl-1,3-cyclobutanediol residues; and
  (ii) 70 to 85 mole % of 1,4-cyclohexanedimethanol residues,
wherein the total mole % of the dicarboxylic acid component is 100 mole %, and the total mole % of the glycol component is 100 mole %; and
about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 97% by weight to about 99.99% by weight of at least one polyester comprising:
(a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and
  (iii) 0 to 30 mole % of residues of at least one modifying aliphatic dicarboxylic acid having up to 16 carbon atoms; and
(b) a glycol component comprising:
  (i) 20 to 30 mole % of 2,2,4,4-tetramethyl-1,3-cyclobutanediol residues; and
  (ii) 70 to 80 mole % of 1,4-cyclohexanedimethanol residues,
wherein the total mole % of the dicarboxylic acid component is 100 mole %, and the total mole % of the glycol component is 100 mole %; and
about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 97% by weight to about 99.99% by weight of at least one polyester comprising:
(a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and
  (iii) 0 to 30 mole % of residues of at least one modifying aliphatic dicarboxylic acid having up to 16 carbon atoms; and
(b) a glycol component comprising:
  (i) 30 to 40 mole % of 2,2,4,4-tetramethyl-1,3-cyclobutanediol residues; and
  (ii) 60 to 70 mole % of 1,4-cyclohexanedimethanol residues,
wherein the total mole % of the dicarboxylic acid component is 100 mole %, and the total mole % of the glycol component is 100 mole %; and
about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend.

In one aspect, the invention relates to a blend comprising about 80% by weight to about 99.99% by weight of at least one polyester comprising:
(a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and
  (iii) 0 to 30 mole % of residues of at least one modifying aliphatic dicarboxylic acid having up to 16 carbon atoms; and
(b) a glycol component comprising:
  (i) 10 to 40 mole % of 2,2,4,4-tetramethyl-1,3-cyclobutanediol residues; and
  (ii) 60 to 90 mole % of 1,4-cyclohexanedimethanol residues,
wherein the total mole % of the dicarboxylic acid component is 100 mole %, and the total mole % of the glycol component is 100 mole %; and
about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 80% by weight to about 99.99% by weight of at least one polyester comprising:
(a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and
  (iii) 0 to 30 mole % of residues of at least one modifying aliphatic dicarboxylic acid having up to 16 carbon atoms; and
(b) a glycol component comprising:
  (i) 15 to 40 mole % of 2,2,4,4-tetramethyl-1,3-cyclobutanediol residues; and
  (ii) 60 to 85 mole % of 1,4-cyclohexanedimethanol residues,
wherein the total mole % of the dicarboxylic acid component is 100 mole %, and the total mole % of the glycol component is 100 mole %; and
about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 80% by weight to about 99.99% by weight of at least one polyester comprising:
(a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and (iii) 0 to 30 mole % of residues of at least one modifying aliphatic dicarboxylic acid having up to 16 carbon atoms; and
(b) a glycol component comprising:
(i) 20 to 40 mole % of 2,2,4,4-tetramethyl-1,3-cyclobutanediol residues; and
(ii) 60 to 80 mole % of 1,4-cyclohexanedimethanol residues,
wherein the total mole % of the dicarboxylic acid component is 100 mole %, and the total mole % of the glycol component is 100 mole %; and
about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 80% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 15 to 30 mole % of 2,2,4,4-tetramethyl-1,3-cyclobutanediol residues; and
(ii) 70 to 85 mole % of 1,4-cyclohexanedimethanol residues,
wherein the total mole % of the dicarboxylic acid component is 100 mole %, and the total mole % of the glycol component is 100 mole %; and
about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 80% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 20 to 30 mole % of 2,2,4,4-tetramethyl-1,3-cyclobutanediol residues; and
(ii) 70 to 80 mole % of 1,4-cyclohexanedimethanol residues,
wherein the total mole % of the dicarboxylic acid component is 100 mole %, and the total mole % of the glycol component is 100 mole %; and
about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 80% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 30 to 40 mole % of 2,2,4,4-tetramethyl-1,3-cyclobutanediol residues; and
(ii) 60 to 70 mole % of 1,4-cyclohexanedimethanol residues,
wherein the total mole % of the dicarboxylic acid component is 100 mole %, and the total mole % of the glycol component is 100 mole %; and
about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 95% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and
(b) a glycol component comprising:
(i) 10 to 40 mole % of 2,2,4,4-tetramethyl-1,3-cyclobutanediol residues; and
(ii) 60 to 90 mole % of 1,4-cyclohexanedimethanol residues,
wherein the total mole % of the dicarboxylic acid component is 100 mole %, and the total mole % of the glycol component is 100 mole %; and
about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 95% by weight to about 99.99% by weight of at least one polyester comprising:
(a) a dicarboxylic acid component comprising:
(i) 70 to 100 mole % of residues of terephthalic acid or an ester thereof;
(ii) 0 to 30 mole % of residues of at least one aromatic dicarboxylic acid having up to 20 carbon atoms; and
(iii) 0 to 30 mole % of residues of at least one modifying aliphatic dicarboxylic acid having up to 16 carbon atoms; and (b) a glycol component comprising:
   (i) 15 to 40 mole % of 2,2,4,4-tetramethyl-1,3-cyclobutanediol residues; and
   (ii) 60 to 85 mole % of 1,4-cyclohexanedimethanol residues,
wherein the total mole % of the dicarboxylic acid component is 100 mole %, and the total mole % of the glycol component is 100 mole %; and
   about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 95% by weight to about 99.99% by weight of at least one polyester comprising:
   (a) a dicarboxylic acid component comprising:
      (i) 70 to 100 mole % of residues of terephthalic acid or an ester thereof;
      (ii) 0 to 30 mole % of residues of at least one aromatic dicarboxylic acid having up to 20 carbon atoms; and
      (iii) 0 to 30 mole % of residues of at least one modifying aliphatic dicarboxylic acid having up to 16 carbon atoms; and
   (b) a glycol component comprising:
      (i) 20 to 40 mole % of 2,2,4,4-tetramethyl-1,3-cyclobutanediol residues; and
      (ii) 60 to 80 mole % of 1,4-cyclohexanedimethanol residues,
   wherein the total mole % of the dicarboxylic acid component is 100 mole %, and the total mole % of the glycol component is 100 mole %; and
   about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 95% by weight to about 99.99% by weight of at least one polyester comprising:
   (a) a dicarboxylic acid component comprising:
      (i) 70 to 100 mole % of residues of terephthalic acid or an ester thereof;
      (ii) 0 to 30 mole % of residues of at least one aromatic dicarboxylic acid having up to 20 carbon atoms; and
      (iii) 0 to 30 mole % of residues of at least one modifying aliphatic dicarboxylic acid having up to 16 carbon atoms; and
   (b) a glycol component comprising:
      (i) 15 to 30 mole % of 2,2,4,4-tetramethyl-1,3-cyclobutanediol residues; and
      (ii) 70 to 85 mole % of 1,4-cyclohexanedimethanol residues,
   wherein the total mole % of the dicarboxylic acid component is 100 mole %, and the total mole % of the glycol component is 100 mole %; and
   about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 95% by weight to about 99.99% by weight of at least one polyester comprising:
   (a) a dicarboxylic acid component comprising:
      (i) 70 to 100 mole % of residues of terephthalic acid or an ester thereof;
      (ii) 0 to 30 mole % of residues of at least one aromatic dicarboxylic acid having up to 20 carbon atoms; and
      (iii) 0 to 30 mole % of residues of at least one modifying aliphatic dicarboxylic acid having up to 16 carbon atoms; and
   (b) a glycol component comprising:
      (i) 20 to 30 mole % of 2,2,4,4-tetramethyl-1,3-cyclobutanediol residues; and
      (ii) 70 to 80 mole % of 1,4-cyclohexanedimethanol residues,
   wherein the total mole % of the dicarboxylic acid component is 100 mole %, and the total mole % of the glycol component is 100 mole %; and
   about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 95% by weight to about 99.99% by weight of at least one polyester comprising:
   (a) a dicarboxylic acid component comprising:
      (i) 70 to 100 mole % of residues of terephthalic acid or an ester thereof;
      (ii) 0 to 30 mole % of residues of at least one aromatic dicarboxylic acid having up to 20 carbon atoms; and
      (iii) 0 to 30 mole % of residues of at least one modifying aliphatic dicarboxylic acid having up to 16 carbon atoms; and
   (b) a glycol component comprising:
      (i) 30 to 40 mole % of 2,2,4,4-tetramethyl-1,3-cyclobutanediol residues; and
      (ii) 60 to 70 mole % of 1,4-cyclohexanedimethanol residues,
   wherein the total mole % of the dicarboxylic acid component is 100 mole %, and the total mole % of the glycol component is 100 mole %; and
   about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 97% by weight to about 99.99% by weight of at least one polyester comprising:
   (a) a dicarboxylic acid component comprising:
      (i) 70 to 100 mole % of residues of terephthalic acid or an ester thereof;
      (ii) 0 to 30 mole % of residues of at least one aromatic dicarboxylic acid having up to 20 carbon atoms; and
      (iii) 0 to 30 mole % of residues of at least one modifying aliphatic dicarboxylic acid having up to 16 carbon atoms; and (b) a glycol component comprising:
  (i) 10 to 40 mole % of 2,2,4,4-tetramethyl-1,3-cyclobutanediol residues; and
  (ii) 60 to 90 mole % of 1,4-cyclohexanedimethanol residues,
wherein the total mole % of the dicarboxylic acid component is 100 mole %, and the total mole % of the glycol component is 100 mole %; and
  about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 97% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 15 to 40 mole % of 2,2,4,4-tetramethyl-1,3-cyclobutanediol residues; and
    (ii) 60 to 85 mole % of 1,4-cyclohexanedimethanol residues,
  wherein the total mole % of the dicarboxylic acid component is 100 mole %, and the total mole % of the glycol component is 100 mole %; and
  about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 97% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 20 to 40 mole % of 2,2,4,4-tetramethyl-1,3-cyclobutanediol residues; and
    (ii) 60 to 80 mole % of 1,4-cyclohexanedimethanol residues,
  wherein the total mole % of the dicarboxylic acid component is 100 mole %, and the total mole % of the glycol component is 100 mole %; and
  about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 97% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 15 to 30 mole % of 2,2,4,4-tetramethyl-1,3-cyclobutanediol residues; and
    (ii) 70 to 85 mole % of 1,4-cyclohexanedimethanol residues,
  wherein the total mole % of the dicarboxylic acid component is 100 mole %, and the total mole % of the glycol component is 100 mole %; and
  about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 97% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 20 to 30 mole % of 2,2,4,4-tetramethyl-1,3-cyclobutanediol residues; and
    (ii) 70 to 80 mole % of 1,4-cyclohexanedimethanol residues,
  wherein the total mole % of the dicarboxylic acid component is 100 mole %, and the total mole % of the glycol component is 100 mole %; and
  about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 97% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and (b) a glycol component comprising:
  (i) 30 to 40 mole % of 2,2,4,4-tetramethyl-1,3-cyclobutanediol residues; and
  (ii) 60 to 70 mole % of 1,4-cyclohexanedimethanol residues,
wherein the total mole % of the dicarboxylic acid component is 100 mole %, and the total mole % of the glycol component is 100 mole %; and
  about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 65%.

In one aspect, the invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 10 to 40 mole % of 2,2,4,4-tetramethyl-1,3-cyclobutanediol residues; and
    (ii) 60 to 90 mole % of 1,4-cyclohexanedimethanol residues,
  wherein the total mole % of the dicarboxylic acid component is 100 mole %, and the total mole % of the glycol component is 100 mole %; and
    about 0.01% by weight to about 20% by weight of at least one antimicrobial agent chosen from at least one of: silver oxides, silver zirconium phosphates, silver glass, silver silicas, or combinations thereof;
  said weight percentages being based on the total weight of the blend;
  wherein said blend has a haze value of less than 50%.

In one aspect, the invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 15 to 40 mole % of 2,2,4,4-tetramethyl-1,3-cyclobutanediol residues; and
    (ii) 60 to 85 mole % of 1,4-cyclohexanedimethanol residues,
  wherein the total mole % of the dicarboxylic acid component is 100 mole %, and the total mole % of the glycol component is 100 mole %; and
    about 0.01% by weight to about 20% by weight of at least one antimicrobial agent chosen from at least one of: silver oxides, silver zirconium phosphates, silver glass, silver silicas, or combinations thereof;
  said weight percentages being based on the total weight of the blend;
  wherein said blend has a haze value of less than 50%.

In one aspect, the invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 20 to 40 mole % of 2,2,4,4-tetramethyl-1,3-cyclobutanediol residues; and
    (ii) 60 to 80 mole % of 1,4-cyclohexanedimethanol residues,
  wherein the total mole % of the dicarboxylic acid component is 100 mole %, and the total mole % of the glycol component is 100 mole %; and
    about 0.01% by weight to about 20% by weight of at least one antimicrobial agent chosen from at least one of: silver oxides, silver zirconium phosphates, silver glass, silver silicas, or combinations thereof;
  said weight percentages being based on the total weight of the blend;
  wherein said blend has a haze value of less than 50%.

In one aspect, the invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 15 to 30 mole % of 2,2,4,4-tetramethyl-1,3-cyclobutanediol residues; and
    (ii) 70 to 85 mole % of 1,4-cyclohexanedimethanol residues,
  wherein the total mole % of the dicarboxylic acid component is 100 mole %, and the total mole % of the glycol component is 100 mole %; and
    about 0.01% by weight to about 20% by weight of at least one antimicrobial agent chosen from at least one of: silver oxides, silver zirconium phosphates, silver glass, silver silicas, or combinations thereof;
  said weight percentages being based on the total weight of the blend;
  wherein said blend has a haze value of less than 50%.

In one aspect, the invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and (b) a glycol component comprising:
  (i) 20 to 30 mole % of 2,2,4,4-tetramethyl-1,3-cyclobutanediol residues; and
  (ii) 70 to 80 mole % of 1,4-cyclohexanedimethanol residues,
wherein the total mole % of the dicarboxylic acid component is 100 mole %, and the total mole % of the glycol component is 100 mole %; and
  about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 80% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 30 to 40 mole % of 2,2,4,4-tetramethyl-1,3-cyclobutanediol residues; and
    (ii) 60 to 70 mole % of 1,4-cyclohexanedimethanol residues,
  wherein the total mole % of the dicarboxylic acid component is 100 mole %, and the total mole % of the glycol component is 100 mole %; and
  about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 95% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 10 to 40 mole % of 2,2,4,4-tetramethyl-1,3-cyclobutanediol residues; and
    (ii) 60 to 90 mole % of 1,4-cyclohexanedimethanol residues,
  wherein the total mole % of the dicarboxylic acid component is 100 mole %, and the total mole % of the glycol component is 100 mole %; and
  about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 95% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 15 to 40 mole % of 2,2,4,4-tetramethyl-1,3-cyclobutanediol residues; and
    (ii) 60 to 85 mole % of 1,4-cyclohexanedimethanol residues,
  wherein the total mole % of the dicarboxylic acid component is 100 mole %, and the total mole % of the glycol component is 100 mole %; and
  about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 95% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 20 to 40 mole % of 2,2,4,4-tetramethyl-1,3-cyclobutanediol residues; and
    (ii) 60 to 80 mole % of 1,4-cyclohexanedimethanol residues,
  wherein the total mole % of the dicarboxylic acid component is 100 mole %, and the total mole % of the glycol component is 100 mole %; and
  about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 95% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and (b) a glycol component comprising:
 (i) 15 to 30 mole % of 2,2,4,4-tetramethyl-1,3-cyclobutanediol residues; and
 (ii) 70 to 85 mole % of 1,4-cyclohexanedimethanol residues,
wherein the total mole % of the dicarboxylic acid component is 100 mole %, and the total mole % of the glycol component is 100 mole %; and
 about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 95% by weight to about 99.99% by weight of at least one polyester comprising:
 (a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and
  (iii) 0 to 30 mole % of residues of at least one modifying aliphatic dicarboxylic acid having up to 16 carbon atoms; and
 (b) a glycol component comprising:
  (i) 20 to 30 mole % of 2,2,4,4-tetramethyl-1,3-cyclobutanediol residues; and
  (ii) 70 to 80 mole % of 1,4-cyclohexanedimethanol residues,
wherein the total mole % of the dicarboxylic acid component is 100 mole %, and the total mole % of the glycol component is 100 mole %; and
 about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 95% by weight to about 99.99% by weight of at least one polyester comprising:
 (a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and
  (iii) 0 to 30 mole % of residues of at least one modifying aliphatic dicarboxylic acid having up to 16 carbon atoms; and
 (b) a glycol component comprising:
  (i) 30 to 40 mole % of 2,2,4,4-tetramethyl-1,3-cyclobutanediol residues; and
  (ii) 60 to 70 mole % of 1,4-cyclohexanedimethanol residues,
wherein the total mole % of the dicarboxylic acid component is 100 mole %, and the total mole % of the glycol component is 100 mole %; and
 about 0.01% by weight to about 5% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 97% by weight to about 99.99% by weight of at least one polyester comprising:
 (a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and
  (iii) 0 to 30 mole % of residues of at least one modifying aliphatic dicarboxylic acid having up to 16 carbon atoms; and
 (b) a glycol component comprising:
  (i) 10 to 40 mole % of 2,2,4,4-tetramethyl-1,3-cyclobutanediol residues; and
  (ii) 60 to 90 mole % of 1,4-cyclohexanedimethanol residues,
wherein the total mole % of the dicarboxylic acid component is 100 mole %, and the total mole % of the glycol component is 100 mole %; and
 about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 97% by weight to about 99.99% by weight of at least one polyester comprising:
 (a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and
  (iii) 0 to 30 mole % of residues of at least one modifying aliphatic dicarboxylic acid having up to 16 carbon atoms; and
 (b) a glycol component comprising:
  (i) 15 to 40 mole % of 2,2,4,4-tetramethyl-1,3-cyclobutanediol residues; and
  (ii) 60 to 85 mole % of 1,4-cyclohexanedimethanol residues,
wherein the total mole % of the dicarboxylic acid component is 100 mole %, and the total mole % of the glycol component is 100 mole %; and
 about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 97% by weight to about 99.99% by weight of at least one polyester comprising:
 (a) a dicarboxylic acid component comprising:
  (i) 70 to 100 mole % of residues of terephthalic acid or an ester thereof;
  (ii) 0 to 30 mole % of residues of at least one aromatic dicarboxylic acid having up to 20 carbon atoms; and
  (iii) 0 to 30 mole % of residues of at least one modifying aliphatic dicarboxylic acid having up to 16 carbon atoms; and (b) a glycol component comprising:
  (i) 20 to 40 mole % of 2,2,4,4-tetramethyl-1,3-cyclobutanediol residues; and
  (ii) 60 to 80 mole % of 1,4-cyclohexanedimethanol residues,
wherein the total mole % of the dicarboxylic acid component is 100 mole %, and the total mole % of the glycol component is 100 mole %; and
  about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 97% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 15 to 30 mole % of 2,2,4,4-tetramethyl-1,3-cyclobutanediol residues; and
    (ii) 70 to 85 mole % of 1,4-cyclohexanedimethanol residues,
wherein the total mole % of the dicarboxylic acid component is 100 mole %, and the total mole % of the glycol component is 100 mole %; and
  about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 97% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 20 to 30 mole % of 2,2,4,4-tetramethyl-1,3-cyclobutanediol residues; and
    (ii) 70 to 80 mole % of 1,4-cyclohexanedimethanol residues,
wherein the total mole % of the dicarboxylic acid component is 100 mole %, and the total mole % of the glycol component is 100 mole %; and
  about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect, the invention relates to a blend comprising about 97% by weight to about 99.99% by weight of at least one polyester comprising:
  (a) a dicarboxylic acid component comprising:
    (i) 70 to 100 mole % of residues of terephthalic acid or an ester thereof;
    (ii) 0 to 30 mole % of residues of at least one aromatic dicarboxylic acid having up to 20 carbon atoms; and
    (iii) 0 to 30 mole % of residues of at least one modifying aliphatic dicarboxylic acid having up to 16 carbon atoms; and
  (b) a glycol component comprising:
    (i) 30 to 40 mole % of 2,2,4,4-tetramethyl-1,3-cyclobutanediol residues; and
    (ii) 60 to 70 mole % of 1,4-cyclohexanedimethanol residues,
wherein the total mole % of the dicarboxylic acid component is 100 mole %, and the total mole % of the glycol component is 100 mole %; and
  about 0.01% by weight to about 3% by weight of at least one antimicrobial agent chosen from at least one of: silver oxides, silver zirconium phosphates, silver glass, silver silicas, or combinations thereof;
said weight percentages being based on the total weight of the blend;
wherein said blend has a haze value of less than 50%.

In one aspect of the invention, each embodiment of the invention can have a haze value of from 0 to 65, or 0 to 60, or 0 to 55, 0 to 50, or 0 to 45, or 0 to 40, or 0 to 35, or 0 to 20, or 0 to 15, or 1 to 20, or 1 to 15, or 5 to 20, or 5 to 15, or 10 to 20, or 10 to 16, or 10 to 15 as determined by ASTM Method D1003 or by other methods described herein. In connection with any one of these haze values, in one embodiment, the percent transmittance of the blend can be at least 50% or at least 60% or at least 70%. In one embodiment, the haze value can be measured on ⅛ thick specimens.

In one aspect of the invention, the blends of the invention can have a haze value of less than 65% at up to 8% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 65% at up to 7% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 65% at up to 6% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 65% at up to 5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 65% at up to 4% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 65% at up to 3% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 65% at up to 2% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 65% at up to 1.5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 65% at up to 1% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 60% at up to 8% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 60% at up to 7% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 60% at up to 6% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 60% at up to 5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 60% at up to 4% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 60% at up to 3% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 60% at up to 2% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 60% at up to 1.5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 60% at up to 1% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 55% at up to 8% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 55% at up to 7% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 55% at up to 6% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 55% at up to 5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 55% at up to 4% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 55% at up to 3% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 55% at up to 2% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 55% at up to 1.5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 55% at up to 1% by weight of at least one antimicrobial agent or antimicrobial additive wherein the haze value is determined by ASTM Method D1003 or by other methods described herein and where the weight percentage of the antimicrobial agent is based on the total weight of the blend.\ In one aspect of the invention, the blends of the invention can have a haze value of less than 50% at up to 8% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 50% at up to 7% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 50% at up to 6% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 50% at up to 5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 50% at up to 4% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 50% at up to 3% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 50% at up to 2% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 50% at up to 1.5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 50% at up to 1% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 40% at up to 4% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 40% at up to 3% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 40% at up to 2% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 40% at up to 1.5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 40% at up to 1% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 30% at up to 4% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 30% at up to 3% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 30% at up to 2% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 30% at up to 1.5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 30% at up to 1% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 20% at up to 4% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 20% at up to 3% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 20% at up to 2% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 20% at up to 1.5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 20% at up to 1% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, each embodiment of the invention can have a b* value of from −10 to 10 or from −5 to 10 or 0 to 10 or −10 or less than 5 or 1 to 5 or 1 to 10 determined as described herein.

These blends provide a unique combination at least two of good clarity, good haze values, good impact strength, good chemical resistance and good microbial resistance.

DETAILED DESCRIPTION

This invention relates to a blend of aliphatic-aromatic polyesters with antimicrobial additives.

More particularly, this invention relates to a blend comprising about 80% by weight to about 99.99% by weight of at least one polyester comprising:
- (a) a dicarboxylic acid component comprising:
  - (i) 70 to 100 mole % of residues of terephthalic acid or an ester thereof;
  - (ii) 0 to 30 mole % of residues of at least one aromatic dicarboxylic acid having up to 20 carbon atoms; and
  - (iii) 0 to 30 mole % of residues of at least one modifying aliphatic dicarboxylic acid having up to 16 carbon atoms; and
- (b) a glycol component comprising:
  - (i) 10 to 40 mole % of 2,2,4,4-tetramethyl-1,3-cyclobutanediol residues; and
  - (ii) 60 to 90 mole % of 1,4-cyclohexanedimethanol residues, wherein the total mole % of the dicarboxylic acid component is 100 mole %, and the total mole % of the glycol component is 100 mole %; and about 0.01% by weight to about 20% by weight of at least one antimicrobial agent chosen from at least one of: silver oxides, silver zirconium phosphates, silver glass, silver silicas, or combinations thereof;

said weight percentages being based on the total weight of the blend.

The term "polyester", as used herein, is intended to include "copolyesters" and is understood to mean a synthetic polymer prepared by the polycondensation of one or more difunctional carboxylic acids with one or more difunctional hydroxyl compounds. Typically the difunctional carboxylic acid is a dicarboxylic acid and the difunctional hydroxyl compound is a dihydric alcohol such as, for example, glycols and diols. The term "residue", as used herein, means any organic structure incorporated into a polymer or plasticizer through a polycondensation reaction involving the corresponding monomer. The term "repeating unit", as used herein, means an organic structure having a dicarboxylic acid residue and a diol residue bonded through a carbonyloxy group. Thus, the dicarboxylic acid residues may be derived from a dicarboxylic acid monomer or its associated acid halides, esters, salts, anhydrides, or mixtures thereof. As used herein, therefore, the term dicarboxylic acid is intended to include dicarboxylic acids and any derivative of a dicarboxylic acid, including its associated acid halides, esters, half-esters, salts, half-salts, anhydrides, mixed anhydrides, or mixtures thereof, useful in a polycondensation process with a diol to make a high molecular weight polyester.

The polyester(s) included in the present invention contain substantially equal molar proportions of acid residues (100 mole %) and diol residues (100 mole %) which react in substantially equal proportions such that the total moles of repeating units is equal to 100 mole %. The mole percentages provided in the present disclosure, therefore, may be based on the total moles of acid residues, the total moles of diol residues, or the total moles of repeating units. For example, a copolyester containing 30 mole % adipic acid, based on the total acid residues, means that the copolyester contains 30 mole % adipic residues out of a total of 100 mole % acid residues. Thus, there are 30 moles of adipic residues among every 100 moles of acid residues. In another example, a copolyester containing 30 mole % 1,6-hexanediol, based on the total diol residues, means that the copolyester contains 30 mole % 1,6-hexanediol residues out of a total of 100 mole % diol residues. Thus, there are 30 moles of 1,6-hexanediol residues among every 100 moles of diol residues.

As used herein, the term "terephthalic acid" is intended to include terephthalic acid itself and residues thereof as well as any derivative of terephthalic acid, including its associated acid halides, esters, half-esters, salts, half-salts, anhydrides, mixed anhydrides, and/or mixtures thereof or residues thereof useful in a reaction process with a diol to make polyester.

In certain embodiments, terephthalic acid or an ester thereof, such as, for example, dimethyl terephthalate or a mixture of terephthalic acid residues and an ester thereof can make up all or a portion of the aromatic dicarboxylic acid component, if any, used to form the polyesters useful in the invention. In certain embodiments, terephthalic acid residues can make up all or a portion of the aromatic dicarboxylic acid component, if any, used to form the polyesters useful in the invention. For purposes of this disclosure, the terms "terephthalic acid" and "dimethyl terephthalate" are used interchangeably herein. In one embodiment, dimethyl terephthalate is part or all of the aromatic dicarboxylic acid component, if any, used to make the polyesters useful in the present invention.

The dicarboxylic acid component of the polyesters useful in the invention can comprise up to 30 mole %, or up to 25 mole %, or up to 20 mole %, or up to 15 mole %, or up to 10 mole %, or up to 5 mole %, or up to 1 mole % of one or more modifying aromatic dicarboxylic acids. Yet another embodiment contains 0 mole % modifying aromatic dicarboxylic acids. Thus, if present, it is contemplated that the amount of one or more modifying aromatic dicarboxylic acids can range from any of these preceding endpoint values including, for example, 0.01 to 10 mole %, from 0.01 to 5 mole % and from 0.01 to 1 mole %. In one embodiment, modifying aromatic dicarboxylic acids that may be used in the present invention include but are not limited to those having up to 20 carbon atoms, and which can be linear, para-oriented, or symmetrical. Examples of modifying aromatic dicarboxylic acids which may be used in this invention include, but are not limited to, isophthalic acid, 4,4'-biphenyldicarboxylic acid, 1,4-, 1,5-, 2,6-, 2,7-naphthalenedicarboxylic acid, and trans-4,4'-stilbenedicarboxylic acid, and esters thereof. In one embodiment, the modifying aromatic dicarboxylic acid is isophthalic acid. The carboxylic acid component of the polyesters useful in the invention can be further modified with up to 30 mole %, up to 20 mole %, up to 10 mole %, up to 5 mole % or up to 1 mole % of one or more aliphatic dicarboxylic acids containing 2-16 carbon atoms, such as, for example, malonic, succinic, glutaric, adipic, pimelic, suberic, azelaic and dodecanedioic dicarboxylic acids, or 1,4-cyclohexanedicarboxylic acid. Certain embodiments can also comprise 0.01 to 40 mole %, 0.01 to 30 mole %, 0.01 to 20 mole %, 0.01 to 10 mole %, 0.1 to 40 mole %, 0.1 to 30 mole %, 0.1 to 20 mole %, 0.1 to 10 mole %, 1 to 40 mole %, 1 to 30 mole %, 1 to 20 mole %, 1 to 10 mole %, 5 to 40 mole %, 5 to 30 mole %, 5 to 20 mole %, or 5 to 10 mole %, of one or more modifying aliphatic dicarboxylic acids. Yet another embodiment contains 0 mole % modifying aliphatic dicarboxylic acids. The total mole % of the dicarboxylic acid component is equal to 100 mole %. In one embodiment, adipic acid and/or glutaric acid are provided in the modifying aliphatic dicarboxylic acid component of the invention.

Esters of dicarboxylic acids or their corresponding esters and/or salts may be used instead of the dicarboxylic acids. Suitable examples of dicarboxylic acid esters include, but are not limited to, the dimethyl, diethyl, dipropyl, diisopropyl, dibutyl, and diphenyl esters. In one embodiment, the esters are chosen from at least one of the following: methyl, ethyl, propyl, isopropyl, and phenyl esters.

For the desired polyester, the molar ratio of cis/trans 2,2,4,4-tetramethyl-1,3-cyclobutanediol can vary from the pure form of each and mixtures thereof. In one embodiment, the molar ratio of cis/trans 2,2,4,4-tetramethyl-1,3-cyclobutanediol can vary within the range of 50/50 to 0/100, for example, between 40/60 to 20/80. In an additional embodiment, the molar ratio of trans/cis 2,2,4,4-tetramethyl-1,3-cyclobutanediol can vary within the range of 50/50 to 0/100, for example, between 40/60 to 20/80.

The cyclohexanedimethanol may be cis, trans, or a mixture thereof, for example, a cis/trans ratio of 60:40 to 40:60 or a cis/trans ratio of 70:30 to 30:70. In one embodiment, the molar ratio of cis/trans 1,4-cyclohexandimethanol can vary within the range of 50/50 to 0/100, for example, between 40/60 to 20/80.

Any of isomers of cyclohexanedimethanol or mixtures thereof may be present in the glycol component of any embodiment of this invention.

In one embodiment, the glycol component of polyesters of the invention can contain 0 to 30 mole % of one or more modifying glycols. In one embodiment, the glycol component of the polymers of the invention can contain 0 to 20 mole % of modifying glycols. In one embodiment, the glycol component of the polyesters of the invention can contain 1 to 20 mole % of one or more modifying glycols. In another embodiment, the glycol component of the polyesters of the invention can contain 25 mole % or less of one or more modifying glycols. In yet another embodiment, the glycol component of the polyesters useful in the invention can contain less than 15 mole % modifying glycols. In one embodiment, the glycol component of the polyesters of the invention can contain less than 10 mole % of one or more modifying glycols. In one embodiment, the glycol component of the polyesters of the invention can contain less than 5 mole % of one or more modifying glycols. In one embodiment, the glycol component of the polyesters of the invention can contain 0.01 to 10 mole % of one or more modifying glycols. In one embodiment, the glycol component of the polyesters of the invention can contain 0 mole % of one or more modifying glycols.

Modifying glycols useful in the polyesters useful in the invention refer to diols other than 2,2,4,4-tetramethyl-1,3-cyclobutanediol and cyclohexanedimethanol and can contain 2 to 16 carbon atoms. Examples of suitable modifying glycols include, but are not limited to, ethylene glycol, diethylene glycol, 1,2-propanediol, 1,3-propanediol, neopentyl glycol, 1,4-butanediol, 1,5-pentanediol, 1,6-hexanediol, polytetramethylene glycol, polyethylene glycol, and/or mixtures thereof. In another embodiment, the modifying glycols include, but are not limited to, at least one of 1,3-propanediol and 1,4-butanediol. In one embodiment, at least one modifying glycol is diethylene glycol. In one embodiment, the diethylene glycol is not added as a separate monomer but is formed during polymerization.

For embodiments of the invention, the polyesters useful in the invention may exhibit at least one of the following inherent viscositiy ranges as determined in 60/40 (wt/wt) phenol/tetrachloroethane at a concentration of 0.25 g/50 ml at 25° C.: 0.35 to 1.2 dL/g; 0.35 to 1 dL/g; 0.35 to 0.80 dL/g; 0.35 to 0.75 dL/g; 0.35 to 0.70 dL/g; 0.35 to less than 0.70 dL/g; 0.35 to 0.68 dL/g; 0.50 to 1.2 dL/g; 0.50 to 1 dL/g; 0.50 to 0.80 dL/g; 0.50 to 0.75 dL/g; 0.50 to less than 0.75 dL/g; 0.50 to 0.70 dL/g; 0.50 to less than 0.70 dL/g; 0.50 to 0.68 dL/g; 0.50 to less than 0.68 dL/g; 0.60 to 1.2 dL/g; 0.60 to 1 dL/g; 0.60 to 0.80 dL/g; 0.60 to 0.75 dL/g; 0.60 to 0.70 dL/g; or 0.60 to 0.68 dL/g;

It is contemplated that the polyesters useful in the invention can possess at least one of the inherent viscosity ranges described herein in combination with either specific or general embodiments of the invention.

The polyesters useful in the blends of the invention can comprise from 0 to 10 mole percent, for example, from 0.01 to 5 mole percent, from 0.01 to 1 mole percent, from 0.05 to 5 mole percent, from 0.05 to 1 mole percent, or from 0.1 to 0.7 mole percent, or from 0.1 to 0.5 mole percent, based on the total mole percentages of either the diol or diacid residues; respectively, of one or more residues of a branching monomer, also referred to herein as a branching agent, having 3 or more carboxyl substituents, hydroxyl substituents, or a combination thereof. In certain embodiments, the branching monomer or agent may be added prior to and/or during and/or after the polymerization of the polyester. The polyester(s) useful in the invention can thus be linear or branched.

Examples of branching monomers include, but are not limited to, multifunctional acids or multifunctional alcohols such as trimellitic acid, trimellitic anhydride, pyromellitic dianhydride, trimethylolpropane, glycerol, pentaerythritol, citric acid, tartaric acid, 3-hydroxyglutaric acid and the like. In one embodiment, the branching monomer residues can comprise 0.1 to 0.7 mole percent of one or more residues chosen from at least one of the following: trimellitic anhydride, pyromellitic dianhydride, glycerol, sorbitol, 1,2,6-hexanetriol, pentaerythritol, trimethylolethane, and/or trimesic acid. The branching monomer may be added to the polyester reaction mixture or blended with the polyester in the form of a concentrate as described, for example, in U.S. Pat. Nos. 5,654,347 and 5,696,176, whose disclosure regarding branching monomers is incorporated herein by reference.

The polyesters useful in the invention can comprise at least one chain extender. Suitable chain extenders include, but are not limited to, multifunctional (including, but not limited to, bifunctional) isocyanates, multifunctional epoxides, including for example, epoxylated novolacs, and phenoxy resins. In certain embodiments, chain extenders may be added at the end of the polymerization process or after the polymerization process. If added after the polymerization process, chain extenders can be incorporated by compounding or by addition during conversion processes such as injection molding or extrusion. The amount of chain extender used can vary depending on the specific monomer composition used and the physical properties desired but is generally about 0.1 percent by weight to about 10 percent by weight, such as about 0.1 to about 5 percent by weight, based on the total weight of the polyester.

The blend of the invention also can contain any amount of any inorganic or organic antimicrobial agent. An antimicrobial agent is an agent or additive or compound that is effective for reducing or retarding or preventing growth of microorganisms including but not limited to bacteria or viruses. In one embodiment, the antimicrobial agent is present in the amount of about 0.01% by weight to about 20% by weight based on the total weight of the blend. In one embodiment, the antimicrobial agent is present in the amount of about 0.25% by weight to about 20% by weight based on the total weight of the blend. In one embodiment, the antimicrobial agent is present in the amount of about 0.25% by weight to about 10% by weight based on the total weight of the blend. In one embodiment, the antimicrobial agent is present in the amount of about 0.5% by weight to about 10% by weight based on the total weight of the blend. In one embodiment, the antimicrobial agent is present in the amount of about 0.01% by weight to about 5% by weight based on the total weight of the blend. In one embodiment, the antimicrobial agent is present in the amount of about 0.5% by weight to about 5% by weight based on the total weight of the blend. In one embodiment, the antimicrobial agent is present in the amount of about 0.01% by weight to about 4% by weight based on the total weight of the blend. In one embodiment, the antimicrobial agent is present in the amount of about 0.25% by weight to about 4% by weight based on the total weight of the blend. In one embodiment, the antimicrobial agent is present in the amount of about 0.01% by weight to about 3% by weight based on the total weight of the blend. In one embodiment, the antimicrobial agent is present in the amount of about 0.25% by weight to about 3% by weight based on the total weight of the blend. In one embodiment, the antimicrobial agent is present in the amount of about 0.01% by weight to about 2% by weight based on the total weight of the blend. In one embodiment, the antimicrobial agent is present in the amount of about 0.25% by weight to about 2% by weight based on the total weight of the blend.

In one aspect of the invention, each embodiment of the invention can have a haze value of from 0 to 65, or 0 to 60, or 0 to 55, or 0 to 50, or 0 to 45, or 0 to 40, or 0 to 35, or 0 to 30, or 0 to 20, or 0 to 15, or 0 to 10, or 0 to 5, or 1 to 20, or 1 to 15, or 5 to 20, or 5 to 15, or 10 to 20, or 10 to 16, or 10 to 15 as determined by ASTM Method D1003 or by other methods described herein. In connection with any one of these haze values, in one embodiment, the percent transmittance of the blend can be at least 50% or at least 60% or at least 70%

In one aspect of the invention, the blends of the invention can have a haze value of less than 65%, or of less than 60%, or of less than 55%, or of less than 50% or of less than 40% or of less than 30% or of less than 20% or of less than 10% at up to 5% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 50% or less than 40% or less than 30% or less than 20% or less than 10% at up to 4% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 65%, or less than 60%, or less than 55%, or less than 50%, or less than 40%, or less than 30% or less than 20% or less than 10% at up to 3% by weight of at least one antimicrobial agent or antimicrobial additive wherein the haze value is determined by ASTM Method D1003 or by other methods described herein and where the weight percentage of the antimicrobial agent is based on the total weight of the blend.

In one aspect of the invention, the blends of the invention can have a haze value of less than 65% or less than 60% or less than 55% or less than 50% or less than 40% or less than 30% or less than 20% or less than 10% at up to 2% by weight of at least one antimicrobial agent or antimicrobial additive wherein the haze value is determined by ASTM Method D1003 or by other methods described herein and where the weight percentage of the antimicrobial agent is based on the total weight of the blend.

Any antimicrobial agent known in the art could be used with the polyester of the invention. One or more antimicrobial agents can be used in the context of the invention.

In certain embodiments, of the invention, examples of suitable inorganic antimicrobial agents can include transition metal ion-based compounds, (e.g., silver, zinc, copper, gold, tin and platinum-based compounds). Examples of suitable silver-containing antimicrobial agents include silver sulfate, silver acetate, silver chloride, silver lactate, silver phosphate, silver stearate, silver thiocyanate, silver proteinate, silver carbonate, silver nitrate, silver sulfadiazine, silver alginate, silver nanoparticles, silver-substituted ceramic zeolites, silver complexed with calcium phosphates, silver-copper complexed with calcium phosphates, silver dihydrogen citrates, silver iodines, silver oxides, silver zirconium phosphates, silver glass, and combinations thereof.

Certain examples of antimicrobial agents can be the following: (1) "AgION": A silver-containing inorganic zeolite food-grade antimicrobial agent, type AJ, which contains 2.5% silver, and which is commercially available under the trade designation "AgION" Antimicrobial from AgION Technologies, Inc., Wakefield, Mass.; (2) "Alphasan": A silver zirconium phosphate, commercially available under the trade designation "ALPHASAN RC 5000" from Milliken Chemicals, Spartanburg, S.C.; (3) "Silver glass": A silver glass antimicrobial agent, commercially available from Giltech, Scotland, UK.; (4) "Copper glass": A copper glass antimicrobial agent, commercially available from Giltech, Scotland, UK; (5) "Silver nanoparticles": A 20% silver nanoparticle dispersion in isopropanol, commercially available under the trade designation "SILVERJET DGP-(I)-20" from Advanced Nano Particles (ANP), Seoul, South Korea; (6) "Silver oxide": Silver oxide (AgO) having a formula weight of 123.9, commercially available from Alfa Aesar, Ward Hill, Mass.; (7) "Ammonium Carbonate": Ammonium carbonate salt, commercially available from Aldrich, Milwaukee, Wis.; (8) "Triclosan": Triclosan antimicrobial agent, commercially available from Ciba Specialty Chemicals., Tarrytown, N.Y.; (9) "DMAEMA-CCl": Dimethylhexadecylammoniumethylmethacrylate-CCl antimicrobial agent, commercially available from Ciba Specialty Chemicals, Tarrytown, N.Y.; (10) "Cosmocil CQ": An antimicrobial agent commercially available under the trade designation "COSMOCIL CQ" from Avecia, Inc., Wilmington Del.; (11) "Vantocil P": A poly (iminoimidocarbonylimidocarbonyliminohexamethylene hydrochloride), commercially available under the trade designation "VANTOCIL P" from Arch Chemicals, Inc., Norwalk, Conn.; (12) "Myacide AS Plus": An antimicrobial agent commercially available under the trade designation "MYACIDE AS PLUS" from BASF Corp., Parsippany, N.J.; (13) "CHG": 20% chlorhexidine gluconate by weight in water, commercially available from Xttrium Laboratories, Inc., Chicago, Ill.; (14) "Bardac 205M": A quaternary ammonium compound commercially available under the trade designation "BARDAC 205M" from Lonza Group Ltd., Valais, Switzerland; (15) "Bardac 208M": A quaternary ammonium compound commercially available under the trade designation "BARDAC 208M" from Lonza Group Ltd., Valais, Switzerland; (16) "3M 906 Hardcoat": A polymerizable precursor commercially available under the trade designation "3M 906" Abrasion Resistant Hardcoat, from 3M Corporation, St. Paul, Minn.; (17) "3M SG composition": A polymerizable precursor commercially available under the trade designation "SCOTCHGARD" UV-curable film protector composition, from 3M Corporation, St. Paul, Minn.; (18) "UVHC3000": A polymerizable precursor commercially available under the trade designation "UVHC3000", from GE Silicones, Waterford, N.Y.; (19) "3M UV-Formulation": A polymerizable precursor containing 13.84 parts of an aliphatic urethane diacrylate diluted with 12% hexanediol diacrylate (commercially available under the trade designation "EBECRYL 284" from UCB Chemicals, Smyma, Ga.), 24.24 parts of isooctylacrylate (available from Sartomer Co., Exton, Pa.), 13.84 parts etrahydrofurfurylacrylate (also available from Sartomer Co.), 5 parts benzophenone free radical-generating photoinitiator (also available from Sartomer Co.), and 5 parts isopropylthioxanthone photoinitiator synergist (available from Aceto Corp., New Hyde Park, N.Y.); (20) "Irgacure 819": A phosphine oxide, phenyl bis(2,4,6-trimethyl benzoyl)) photoinitiator, commercially available under the trade designation "IRGACURE 819", from Ciba Specialty Chemicals, Tarrytown, N.Y.; (21) "Lauricidin": A glycerol monolaurate fatty acid monoester, commercially available under the trade designation "LAURICIDIN" from Med-Chem Laboratories, East Lansing, Mich. [0091]"DOSS surfactant": A dioctylsulfosuccinate (DOSS) surfactant, commercially available from Alfa Aesar, Ward Hill, Mass.; (22) "Salicylic acid": A 2-hydroxybenzoic acid (HOC6HgCO2H) with a formula weight of 138.1, commercially available from Sigma-Aldrich Chemical Company, Saint Louis, Mo.; (23) "Select Silver" antimicrobial agents commercially available from Milliken Chemical Company, Spartanburg, S.C.; (24) "Hygentic" antimicrobial additives commercially available from BASF Corporation, Tarrytown, N.Y.; or (25) Agion SL antimicrobial additive Wakefield, Mass.

In one embodiment, the antimicrobial agent can be chosen from at least one of: silver oxides, silver zirconium phosphates, silver glass, silver silicas, or combinations thereof. In one embodiment, the antimicrobial agent or additive is a silver oxide. In one embodiment, the antimicrobial agent or additive can be silver magnesium silica, optionally having an average particle size of around 40 microns, although similar additive types with differing particle sizes can be used. The glass transition temperature (Tg) of the polyesters useful in the invention, if measured, was determined using a TA DSC 2920 from Thermal Analyst Instrument at a scan rate of 20° C./min. In one embodiment of the invention, the Tg of the polyester can be 90 to 150° C., 90 to 140° C., or 90 to 130° C., or 90 to 120° C., or 100 to 140° C., or 100 to 130° C., or 100 to 120° C.

In one embodiment, certain polyesters useful in this invention can be visually clear. The term "visually clear" is defined herein as a low amount of cloudiness, haziness, and/or muddiness, when inspected visually.

In one embodiment, the molded samples of blends of the invention can be measured for optical (color and haze) using a Hunterlab Ultrascan Vis having a 10° observer in transmission mode. Color and haze can be measured using the following configuration: Transmittance Mode, D65 Light Source (Daylight, Noon World Average, 6500° K color temperature), 10° standard observer, large area view (1" diameter), and specular included.

In another embodiment, molded samples of blends of the invention can be measured for optical (color and haze) using ASTM D 1003. In one embodiment, these measurements can be performed on ⅛ inch width samples. In another embodiment, these measurements are performed on ⅛ inch width samples.

The term "refractive index" (abbreviated herein as "RI") as used herein, refers to refractive index measurements obtained according to standard methods well known in the art. The refractive indices reported herein were determined at a wavelength of 633 nm using a Metricon Prism Coupler™ model 2010 refractometer (available from Metricon Inc.) and are reported as the average of the refractive indices measured in 3 orthogonal directions (extrusion or stretch, transverse, and thickness directions). In one embodiment, the refractive index of the polyesters of the invention can be 1.48 to 1.58. In one embodiment, the refractive index of the antimicrobial additive can also be 1.48 to 1.58. In one embodiment, the difference in refractive index between the polyesters useful in the invention and the antimicrobial additive can also be between about 0.04 to about −0.04, or about 0.02 to about −0.02.

The term "% haze", as used herein, refers to haze values determined according to ASTM Method D1003 using a HunterLab UltraScan Sphere 8000 Colorimeter manufactured by Hunter Associates Laboratory, Inc., Reston, Va. using Hunter's Universal Software (version 3.8) (% Haze=100*Diffuse Transmission/Total Transmission). For the compositions of the invention, haze is determined by molding or casting the composition into a sheet or film having a thickness of ⅛ inch or less and measuring the haze according to D1003 and/or the procedure described in the examples. For shaped articles, including multilayer shaped articles, the haze can be determined by cutting out a small (i.e., 1×1 cm) section of the article, having a thickness of ⅛ inch or less, and measuring the haze according the procedure described herein. Again in one embodiment, these measurements can be performed on ⅛ inch width samples. In another embodiment, these measurements are performed on ⅛ inch width samples.

In one embodiment, the polyester blends of the invention, [in one embodiment, in the presence of and/or in the absence of toner(s)], can have color values L*, a* and b* which can be determined using a Hunter Lab Ultrascan Spectra Colorimeter manufactured by Hunter Associates Lab Inc., Reston, Va. The color determinations are averages of values measured on either pellets of the polyesters or plaques or other items injection molded or extruded from them. They are determined by the L*a*b* color system of the CIE (International Commission on Illumination) (translated), wherein L* represents the lightness coordinate, a* represents the red/green coordinate, and b* represents the yellow/blue coordinate. In certain embodiments, the b* values for the polyesters useful in the invention [in one embodiment, in the presence of and/or in the absence of toner(s)] can be from −12 to less than 12 and the L* values can be from 50 to 90. In other embodiments, the b* values for the polyesters useful in the invention [in one embodiment, in the presence of and/or in the absence of toner(s)] can be present in one of the following ranges: from −10 to 10; −10 to less than 10; −10 to 9; −10 to 8; −10 to 7; −10 to 6; −10 to 5; −10 to 4; −10 to 3; −10 to 2; from −5 to 9; −5 to 8; −5 to 7; −5 to 6; −5 to 5; −5 to 4; −5 to 3; −5 to 2; 0 to 9; 0 to 8; 0 to 7; 0 to 6; 0 to 5; 0 to 4; 0 to 3; 0 to 2; 1 to 10; 1 to 9; 1 to 8; 1 to 7; 1 to 6; 1 to 5; 1 to 4; 1 to 3; and 1 to 2. In other embodiments, the L* value for the polyesters useful in the invention can be present in one of the following ranges: 50 to 60; 50 to 70; 50 to 80; 50 to 90; 60 to 70; 60 to 80; 60 to 90; 70 to 80; 79 to 90.

Notched Izod impact strength, as described in ASTM D256, is a common method of measuring toughness. Notched Izod impact strength is measured herein at 23° C. with a 10-mil notch in a 3.2 mm (⅛-inch) thick bar determined according to ASTM D256. In one embodiment, certain polyesters useful in the invention can exhibit a notched Izod impact strength of at least 1/2 ft-lb/in at 23° C. with a 10-mil notch in a 3.2 mm (⅛-inch) thick bar determined according to ASTM D256. In one embodiment, certain polyesters useful in the invention can exhibit a notched Izod impact strength of at least 1 ft-lb/in at 23° C. with a 10-mil notch in a 3.2 mm (⅛-inch) thick bar determined according to ASTM D256. In one embodiment, certain polyesters useful in the invention can exhibit a notched Izod impact strength of at least 2 ft-lb/in at 23° C. with a 10-mil notch in a 3.2 mm (⅛-inch) thick bar determined according to ASTM D256. In one embodiment, certain polyesters useful in the invention can exhibit a notched Izod impact strength of at least 3 ft-lb/in at 23° C. with a 10-mil notch in a 3.2 mm (⅛-inch) thick bar determined according to ASTM D256. In one embodiment, certain polyesters useful in the invention can exhibit a notched Izod impact strength of at least 4 ft-lb/in at 23° C. with a 10-mil notch in a 3.2 mm (⅛-inch) thick bar determined according to ASTM D256. In one embodiment, certain polyesters useful in the invention can exhibit a notched Izod impact strength of at least 5 ft-lb/in at 23° C. with a 10-mil notch in a 3.2 mm (⅛-inch) thick bar determined according to ASTM D256. In another embodiment, certain polyesters useful in the invention can exhibit a notched Izod impact strength of at least 7.5 ft-lb/in at 23° C. with a 10-mil notch in a 3.2 mm (⅛-inch) thick bar determined according to ASTM D256. In one embodiment, certain polyesters useful in the invention can exhibit a notched Izod impact strength of at least 10 ft-lb/in at 23° C. with a 10-mil notch in a 3.2 mm (⅛-inch) thick bar determined according to ASTM D256.

Certain polyester(s) or blends of the invention have improved environmental stress cracking resistance. Generally, environmental stress cracking resistance testing according to the present invention is described in R. L. Bergen, Jr., SPE J. 667-670 (1962) entitled "Stress cracking of rigid thermoplastics". Certain polyester(s) and/or blends of the invention can have a lipid critical strain of at least 0.6% or at least 0.7% or at least 0.8% or at least 0.9% or of greater than 0.9%. Certain polyester(s) and/or polyester blends of the invention can have an isopropanol critical strain of at least 0.9% or at least 1.0% or of greater than 1.0%. Certain polyester(s) and/or polyester blends of the invention can have a lipid critical strain of at least 0.9% and an isopropanol critical strain of greater than 1.0%. Lipid critical strain and/or isopropanol critical strain can be measured as described in in R. L. Bergen, Jr., SPE J. 667-670 (1962) entitled "Stress cracking of rigid thermoplastics".

In one embodiment, phosphorus compound(s) can be useful in the invention and can be an organic compound such as, for example, a phosphorus acid ester containing halogenated or non-halogenated organic substituents. The phosphorus compound(s) useful in the invention can comprise a wide range of phosphorus compounds well-known in the art such as, for example, phosphines, phosphites, phosphinites, phosphonites, phosphinates, phosphonates, phosphine oxides, and phosphates.

In one embodiment, the phosphorus compounds useful in the invention include but are not limited to alkyl, aryl or mixed alkyl aryl esters or partial esters of phosphoric acid, phosphorus acid, phosphinic acid, phosphonic acid, or phosphonous acid. The alkyl or aryl groups can contain one or more substituents.

The esters can contain alkyl, branched alkyl, substituted alkyl, alkyl ethers, aryl, and/or substituted aryl groups. The esters can also have at least one alkyl group and at least one aryl group. The number of ester groups present in the particular phosphorus compound can vary from zero up to the maximum allowable based on the number of hydroxyl groups present on the phosphorus compound used. For example, an alkyl phosphate ester can include one or more of the mono-, di-, and tri alkyl phosphate esters; an aryl phosphate ester includes one or more of the mono-, di-, and tri aryl phosphate esters; and an alkyl phosphate ester and/or an aryl phosphate ester also include, but are not limited to, mixed alkyl aryl phosphate esters having at least one alkyl and one aryl group.

In one aspect, the phosphorus compounds useful in the invention can comprise at least one phosphorus compound chosen from at least one of substituted or unsubstituted alkyl phosphate esters, substituted or unsubstituted aryl phosphate esters, substituted or unsubstituted mixed alkyl aryl phosphate esters, diphosphites, salts of phosphoric acid, phosphine oxides, and mixed aryl alkyl phosphites, reaction products thereof, and mixtures thereof. The phosphate esters include esters in which the phosphoric acid is fully esterified or only partially esterified.

Catalysts useful in making the polyesters useful in the invention can include, but are not limited to, those based on gallium, zinc, antimony, cobalt, manganese, magnesium, germanium, lithium, tin, titanium, aluminum compounds, and an aluminum compound with lithium hydroxide or sodium hydroxide. In one embodiment, the catalyst can be a combination of at least one tin compound and at least one titanium compound. In one embodiment, the catalyst can be at least one tin compound. In another embodiment, the catalyst can be at least one titanium compound.

In one embodiment, catalyst amounts can range from 10 ppm to 20,000 ppm or 10 to 10,000 ppm, or 10 to 5000 ppm or 10 to 1000 ppm or 10 to 500 ppm, or 10 to 300 ppm or 10 to 250 ppm based on the catalyst metal and based on the weight of the final polymer. The process can be carried out in either a batch or continuous process. In one embodiment, the process is carried out in a continuous process.

In one embodiment, the polymers useful in the invention can be prepared by a process comprising the steps of:
(A) heating a mixture comprising the monomers useful in the polyesters useful in the invention in the presence of at least one tin catalyst at a temperature of 150 to 250° C. for a time sufficient to produce an initial polyester;
(B) polycondensing the product of Step (A) by heating it at a temperature of 230 to 320° C. for 1 to 12 hours; and
(C) removing any unreacted glycols.

Reaction times for the esterification Step (A) are dependent upon the selected temperatures, pressures, and feed mole ratios of glycol to dicarboxylic acid.

Typically, Step (B) and Step (C) can be conducted at the same time. These steps can be carried out by methods known in the art such as by placing the reaction mixture under a pressure ranging, from 0.002 psig to below atmospheric pressure, or by blowing hot nitrogen gas over the mixture.

The polyesters of the present invention can also be prepared by any other procedures known to persons skilled in the art. The reaction of the diol and dicarboxylic acid may be carried out using conventional polyester polymerization conditions or by melt phase processes, but those with sufficient crystallinity may be made by melt phase followed by solid phase polycondensation techniques. Stirring or appropriate conditions are used in both stages to ensure adequate heat transfer and surface renewal of the reaction mixture.

The invention further relates to a blend optionally containing an additional polymeric component. The blend can comprise:
(a) from 80 to 99.99 weight % of the polyesters useful in the invention;
(b) 0 up to 19.99 weight % of at least one additional polymeric components; and (c) 0.01 to 20% by weight; said weight percentages being based on the total weight of the blend.

The invention further relates to a blend optionally containing an additional polymeric component. The blend can comprise:
(b) from 80 to 99.99 weight % of the polyesters useful in the invention;
(b) 0.01 up to 19.98 weight % of at least one additional polymeric components; and (c) 0.01 to 20% by weight; said weight percentages being based on the total weight of the blend.

Suitable examples of the additional polymeric components include, but are not limited to, nylon; polyesters other than the ones as described specifically herein as being useful in the invention; polyamides such as ZYTEL® from DuPont; polystyrene; polystyrene copolymers; styrene acrylonitrile copolymers; acrylonitrile butadiene styrene copolymers; poly(methylmethacrylate); acrylic copolymers; poly(ether-imides) such as ULTEM® (a poly(ether-imide) from General Electric); polyphenylene oxides such as poly(2,6-dimethylphenylene oxide) or poly(phenylene oxide)/polystyrene blends such as NORYL 1000® (a blend of poly(2,6-dimethylphenylene oxide) and polystyrene resins from General Electric); polyphenylene sulfides; polyphenylene sulfide/sulfones; poly(ester-carbonates); polycarbonates such as LEXAN® (a polycarbonate from General Electric); polysulfones; polysulfone ethers; and poly(ether-ketones) of aromatic dihydroxy compounds; or mixtures of any of the foregoing polymers.

In addition, the blends of the invention may also contain common additives such as colorants, toner(s), dyes, mold release agents, flame retardants, plasticizers, nucleating agents, stabilizers, and antioxidants, including but not limited to, UV stabilizers, thermal stabilizers other than the phosphorus compounds describe herein, and/or reaction products thereof, fillers, and impact modifiers. In one embodiment, the blends can contain from 0.01 to 25% by weight of one or more of these additives. Examples of typical commercially available impact modifiers well known in the art and useful in this invention include, but are not limited to, ethylene/propylene terpolymers, functionalized polyolefins such as those containing methyl acrylate and/or glycidyl methacrylate, styrene-based block copolymeric impact modifiers, and various acrylic core/shell type impact modifiers. Residues of such additives are also contemplated as part of the polyester composition.

In addition, certain agents which colorize the polymer can be added to the melt. In one embodiment, a bluing toner is added to the melt in order to reduce the b* of the resulting polyester polymer melt phase product. Such bluing agents include blue inorganic and organic toner(s). In addition, red toner(s) can also be used to adjust the a* color. Organic toner(s), e.g., blue and red organic toner(s), such as those toner(s) described in U.S. Pat. Nos. 5,372,864 and 5,384,377, which are incorporated by reference in their entirety, can be used. The organic toner(s) can be fed as a premix composition. The premix composition may be a neat blend of the red and blue compounds or the composition may be pre-dissolved or slurried in one of the polyester's raw materials, e.g., ethylene glycol.

The total amount of toner components added depends, of course, on the amount of inherent yellow color in the base polyester and the efficacy of the toner. Generally, in one embodiment, a concentration of up to about 15 ppm of combined organic toner components and a minimum concentration of about 0.5 ppm can be used. The total amount of bluing additive typically ranges from 0.5 to 10 ppm.

The toner(s) can be added to the esterification zone or to the polycondensation zone. Preferably, the toner(s) are added to the esterification zone or to the early stages of the polycondensation zone, such as to a prepolymerization reactor The aliphatic polyester composition of the invention also can comprise at least one hindered amine light stabilizer, abbreviated herein as "HALS". Many of the HALS useful in the present invention are known compounds and some are commercially available. The HALS can include their salts, N-oxides N-hydroxides. In general, the HALS can be described as having an amino nitrogen contained in a carbonnitrogen-carbon chain which forms part of a non-aromatic heterocyclic ring where each of the two carbon atoms of the chain is bonded to two lower alkyl groups which may be the same or different, each lower alkyl group containing from 1 to 22 carbon atoms, or to an alicyclic group containing from 3 to 8 carbon atoms, which sterically hinder the amine. For example, in one embodiment of the invention, the HALS can comprise 2,2,6,6-tetraalkylpiperidines, their acid addition salts or complexes with metal compounds.

Ultraviolet light absorbers (UVAs) can also be included in the polyester blends of the invention. In one embodiment, the term "ultraviolet light absorber" is defined as one compound or a mixture of compounds that absorb light in the range of 290-400 nm with a minimal absorbance between 400 and 700 nm, and that improves the weatherability of the polymer compositions. In accordance with the present invention, the aliphatic polyesters of the present invention can have blended therein at least one UVA selected from triazines, cyanoacrylates, benzotriazoles, naphthalenes, and benzoxazinones and mixtures thereof. Such materials are described in greater detail in U.S. Pat. Nos. 6,352,783, 5,480,926 and 5,783,307, and United States Publication 2006/0111481 published on May 25, 2006.

Within the scope of this invention are commercially available UVAs such as, for example: Cyasorb UV-2337 (Cytec Industries, CAS#25973-55-1), Cyasorb UV-5411 (Cytec Industries, CAS#3147-75-9), Cyasorb UV-5365 (Cytec Industries, CAS#2440-22-4), Cyasorb UV-1164 (Cytec Industries, CAS#2725-22-6), Cyasorb UV-3638 (Cytec Industries, CAS#18600-59-4), Tinuvin 213 (Ciba Specialty Chemicals, CAS#104810-47-1), Tinuvin 234 (Ciba Specialty Chemicals, CAS#70321-86-7), Tinuvin 320 (Ciba Specialty Chemicals, CAS#3846-71-7), Tinuvin 326 (Ciba Specialty Chemicals, CAS#3896-11-5), Tinuvin 327 (Ciba Specialty Chemicals, CAS#3864-99-1), Tinuvin 328 (Ciba Specialty Chemicals, CAS#25973-55-1), Tinuvin 329 (Ciba Specialty Chemicals, CAS#3147-75-9), Tinuvin 350 (Ciba Specialty Chemicals, CAS#36437-37-3), Tinuvin 360 (Ciba Specialty Chemicals, CAS#103597-45-1), Tinuvin 571 (Ciba Specialty Chemicals, CAS#23328-53-2) and Tinuvin 1577 (Ciba Specialty Chemicals, CAS#147315-50-2). In one embodiment, the UVAs are chosen from benzotriazoles, triazines and benzoxazin-4-ones such as Cyasorb UV-1164 (Cytec Industries, CAS#2725-22-6), Cyasorb UV-3638 (Cytec Industries, CAS#18600-59-4), Tinuvin 1577 (Ciba Specialty Chemicals, CAS#147315-50-2), Tinuvin 234 (Ciba Specialty Chemicals, CAS#70321-86-7) and Tinuvin 328 (Ciba Specialty Chemicals, CAS#25973-55-1). In another embodiment, the UVAs are chosen from Cyasorb UV-1164 (Cytec Industries, CAS#2725-22-6), Cyasorb UV-3638 (Cytec Industries, CAS#18600-59-4) and Tinuvin 1577 (Ciba Specialty Chemicals, CAS#147315-50-2. A combination of two or more of any of the UVAs may be used within the scope of this invention.

The blends of the present invention can contain one or more compounds chosen from phenolic antioxidants, hindered phenols, phosphite stabilizers, phosphonite stabilizers and other stabilizers known to one skilled in the art.

The terms "phenolic antioxidants" and "hindered phenol" are primary antioxidants that are known to those skilled in the art and may be represented by the structures listed on pages 98-108 in the *Plastic Additives Handbook 5$^{th}$ Edition* (Hanser Gardner Publications, Inc., Cincinnati, Ohio, USA, 2001), incorporated herein by reference in its entirety. Some common phenolic antioxidants are as follows: Irganox 1010 (Ciba Specialty Chemicals, CAS#6683-19-8), Irganox 1330 (Ciba Specialty Chemicals, CAS#1709-70-2) and Irganox 3114 (Ciba Specialty Chemicals, CAS#27676-62-6).

The terms "phosphite stabilizers" and "phosphonite stabilizers" refer to secondary antioxidants that are known to those skilled in the art and may be represented by the structures listed on pages 109-112 in the *Plastic Additives Handbook 5$^{th}$ Edition* (Hanser Gardner Publications, Inc., Cincinnati, Ohio, USA, 2001), incorporated herein by reference in its entirety. Some common phosphite stabilizers are as follows: Ultranox 626 (GE Specialty Chemicals, CAS#26741-53-7), Irgafos 168 (Ciba Specialty Chemicals, CAS#31570-04-4), Weston 619 (GE Specialty Chemicals, CAS#3806-34-6) and Doverphos S-9228 (Dover Chemicals, CAS#154862-43-8).

For example, in one embodiment of the invention, alkyl phosphites (for example Weston 619) may be combined with an ultraviolet light absorber. For example, in one embodiment of the invention, aryl phosphites (for example, Irgafos 168) can be combined with a hindered amine light stabilizer and optionally, an ultraviolet light absorber. For example, in one embodiment, phenolic antioxidants (for example, Irganox 1010) can be added during melt processing. Phenolic antioxidants are particularly useful when a polyglycol ether [for example, poly(tetramethylene glycol)] is present.

The various components of the blends of the invention may be blended or mixed in any manner known in the art including but not limited to batch, semicontinuous, or continuous processes.

Commercial applications of interest to this technology include but are not limited to medical devices such as luers, tubing, intravenous components, needle-free valves, connectors, and various other devices where clarity of parts is desired. In addition, medical packaging and food packaging are other areas where the technology has applicability.

The technology can also be used in applications including but not limited to blender housings, sports bottles, water bottles, 5 gallon water containers, ice machine parts, and/or other parts where both clarity and antimicrobial additives are desired.

This invention can be further illustrated by the following examples of preferred embodiments thereof, although it will be understood that these examples are included merely for purposes of illustration and are not intended to limit the scope of the invention unless otherwise specifically indicated.

EXAMPLES

Sample Preparation

Samples were prepared by blending (1) a aliphatic-aromatic

Examples

Sample Preparation

Samples were prepared by blending by blending an aliphaticaromatic copolyester with an antimicrobial additive. The additive used for this work is a silver magnesium silica complex (SR12). This particular additive is sold by Milliken Chemical Company as Select Silver® SR12 antimicrobial agent. The scope of this invention is not limited to this additive specifically as other additives such as Agion's SL silver glass additive or BASF's HyGentic 6000 and 7000 products could be used as well as others. The polymers used for this study are aromatic-aliphatic polymer A (AAP-A), aromatic-aliphatic polymer B (AAP-B), aromatic-aliphatic polymer C (AAP-C), aromatic-aliphatic polymer D (AAP-D), aromatic-aliphatic polymer E (AAP-E). AAP-A is a copolyester having 100 mole percent terephthalic acid residues, 31 mole percent 1,4-cyclohexanedimethanol residues, and 69 mole percent ethylene glycol residues and the polymer has a specific gravity of 1.27. AAP-B is a copolyester having 100 mole percent terephthalic acid residues, 62 mole percent 1,4-cyclohexanedimethanol residues, and 38 mole percent ethylene glycol residues and the polymer has a specific gravity of 1.23. AAP-C is a copolyester having 100 mole percent terephthalic acid residues, 81 mole percent 1,4-cyclohexanedimethanol residues, and 19 mole percent ethylene glycol residues and the polymer has a specific gravity of 1.20. AAP-D is a copolyester having 100 mole percent terephthalic acid residues, 78 mole percent 1,4-cyclohexanedimethanol residues, and 22 mole percent 2,2,4,4,-tetramethyl-1,3-cyclobutanediol residues and the polymer has specific gravity of 1.18. AAP-E is a copolyester having 100 mole percent terephthalic acid residues, 65 mole percent 1,4-cyclohexanedimethanol residues, and 35 mole percent 2,2,4,4,-tetramethyl-1,3-cyclobutanediol residues and the polymer has specific gravity of 1.17

TABLE 1

| Example | Polymer Type | SR 12 (wt %) | Haze (%) |
|---|---|---|---|
| CE #1 | AAP-A | 0% | 2.31 |
| CE #2 | AAP-A | 2% | 76.61 |
| CE #3 | AAP-A | 5% | 93.22 |
| CE #4 | AAP-A | 10% | 97.68 |
| CE #5 | AAP-B | 0% | 1.34 |
| CE #6 | AAP-B | 2% | 66.27 |
| CE #6 | AAP-B | 5% | 88.63 |
| CE #8 | AAP-B | 10% | 96.03 |
| CE #9 | AAP-C | 0% | 1.67 |
| CE #10 | AAP-C | 2% | 60.19 |
| CE #11 | AAP-C | 5% | 85.22 |
| CE #12 | AAP-C | 10% | 94.86 |
| EX #1 | AAP-D | 0% | 1.18 |
| EX #2 | AAP-D | 2% | 34.93 |
| EX #3 | AAP-D | 5% | 63.33 |
| EX #4 | AAP-D | 10% | 84.66 |
| EX #5 | AAP-E | 0% | 1.35 |
| EX #6 | AAP-E | 2% | 23.43 |
| EX #7 | AAP-E | 5% | 54.06 |

Compounding

The materials were dried separately in a desiccant drying system. Aliphatic-aromatic polyesters (AAP-A, AAP-B, AAP-C) were dried at 65 degree celsius for 8 hours and aliphatic-aromatic polyesters (AAP-D, AAP-E,) were dried at 85 degree celsius for 8 hours. The antimicrobial additive was not dried prior to compounding. The aliphatic-aromatic copolyester was bag blended with the antimicrobial additive. Blended samples were compounded on a 30 mm Werner Pfleiderer co-rotating twin screw extruder. A "medium shear" screw configuration was used. The barrel zone temperatures were set 260 degrees celsius except for Zone 1A and Zone 1B which were set at 180 and 200 degrees celsius respectively. The feed zone was cooled with circulating water and the die that was set at 260 degrees celsius. The screw speed was 350 rpm and torque outputs on the machine ranged between 70 and 100 percent. All materials were fed at barrel zone 1 of the twin screw. The extrudate from the twin screw was forced through a pelletizing rod die which forms a strand that was cooled by a water bath. The first 5 minutes of extrudate was not collected in order to ensure the extruder had been adequately purged. Samples were collected after the strands were quenched in a water bath and chopped into pellets.

Injection Molding

The compounded materials were dried separately in a desiccant drying system. Compounded aliphatic-aromatic polyesters (AAP-A, AAP-B, AAP-C) were dried at 65 degree celsius for 8 hours and compounded aliphatic-aromatic polyesters (AAP-D, AAP-E,) were dried at 85 degree celsius for 8 hours. After drying, the materials were injection molded into tensile bars, flex bars, and plaques. For comparative examples (1-12) and examples (1-7), the plaques specimens are 101 mm long by 101 mm wide by 3.2 mm thick. The materials were molded on a Toyo 90 molding machine. Compounded aliphatic-aromatic polyesters (AAP-A, AAP-B, AAP-C) were molded on a Toyo 90 molding machine that had the $1^{st}$ zone set at 238 degrees celsius with the remaining zones at 249 degrees celsius. Parts of compounded aliphatic-aromatic polyester (AAP-D) were made on a Toyo 90 molding machine that had the $1^{st}$ zone set at 265 degrees celsius with the remaining zones at 277 degrees celsius. Parts of compounded aliphatic-aromatic polyester (AAP-E) were made on a Toyo 90 molding machine that had the zones set at 280 degrees celsius. For compounded aliphatic-aromatic polyesters (AAP-A, AAP-B, AAP-C), the mold temperature was set at 21 degrees celsius. For compounded aliphatic-aromatic polyesters (AAP-D, AAP-E), the mold temperature was set at 43 degrees celsius. All molded materials had an overall cycle time between 35 and 40 seconds.

The molded samples were then measured for optical (color and haze) using a Hunterlab Ultrascan V is having a 10° observer in transmission mode. Color and haze were measured using the following configuration: Transmittance Mode, D65 Light Source (Daylight, Noon World Average, 6500° K color temperature), 10° standard observer, large area view (1" diameter), and specular included.

Comparative Example 1

100 weight percent of AAP-A containing no antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 2

98 weight percent of AAP-A containing 2 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 3

95 weight percent of AAP-A containing 5 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 4

90 weight percent of AAP-A containing 10 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 5

100 weight percent of AAP-B containing no antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 6

98 weight percent of AAP-B containing 2 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 7

95 weight percent of AAP-B containing 5 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 8

90 weight percent of AAP-B containing 10 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 9

100 weight percent of AAP-C containing no antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 10

98 weight percent of AAP-C containing 2 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 11

95 weight percent of AAP-C containing 5 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Comparative Example 12

90 weight percent of AAP-C containing 10 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Example 1

100 weight percent of AAP-D containing no antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Example 2

98 weight percent of AAP-D containing 2 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Example 3

95 weight percent of AAP-D containing 5 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Example 4

90 weight percent of AAP-D containing 10 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Example 5

100 weight percent of AAP-E containing no antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Example 6

98 weight percent of AAP-E containing 2 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

Example 7

95 weight percent of AAP-E containing 5 weight percent of an antimicrobial additive was pelletized on a Werner Pfleiderer twin screw extruder and then molded into 101 mm*101 mm*3.2 mm plaques on a Toyo 90 molding machine. The plaques were measured on a Hunterlab Ultrascan V is to determine color and haze. The data can be observed in Table 1.

SUMMARY

For Table 1, Examples (1-7) show that clarity can be achieved in the aromatic-aliphatic polyesters (AAP-D and AAP-E) to a much higher degree relative to other aromatic-aliphatic polyesters (AAP-A, AAP-B, and AAP-C).

The invention has been described in detail with reference to the embodiments disclosed herein, but it will be understood that variations and modifications can be effected within the spirit and scope of the invention.

We claim:

1. A blend comprising about 80% by weight to about 99.99% by weight of at least one polyester comprising:
   (a) a dicarboxylic acid component comprising:
      (i) 70 to 100 mole % of residues of terephthalic acid or an ester thereof;
      (ii) 0 to 30 mole % of residues of at least one aromatic dicarboxylic acid having up to 20 carbon atoms; and
      (iii) 0 to 30 mole % of residues of at least one modifying aliphatic dicarboxylic acid having up to 16 carbon atoms; and
   (b) a glycol component comprising:
      (i) 10 to 40 mole % of 2,2,4,4-tetramethyl-1,3-cyclobutanediol residues; and
      (ii) 60 to 90 mole % of 1,4-cyclohexanedimethanol residues,
   wherein the total mole % of the dicarboxylic acid component is 100 mole %, and the total mole % of the glycol component is 100 mole %; and
   about 0.01% by weight to about 20% by weight of at least one antimicrobial agent chosen from at least one of: silver oxides, silver zirconium phosphates, silver glass, silver silicas, or combinations thereof;
said weight percentages being based on the total weight of the blend.

2. The blend of claim 1 wherein the glycol component of the polyester comprises:
   i) 15 to 40 mole % of 2,2,4,4-tetramethyl-1,3-cyclobutanediol residues; and
   ii) 60 to 85 mole % of 1,4-cyclohexanedimethanol residues.

3. The blend of claim 1 wherein the glycol component of the polyester comprises:
   i) 15 to 30 mole % of 2,2,4,4-tetramethyl-1,3-cyclobutanediol residues; and
   ii) 70 to 85 mole % of 1,4-cyclohexanedimethanol residues.

4. The blend of claim 1 wherein the glycol component of the polyester:
   i) 20 to 40 mole % of 2,2,4,4-tetramethyl-1,3-cyclobutanediol residues; and
   ii) 60 to 80 mole % of 1,4-cyclohexanedimethanol residues.

5. The blend of claim 1 wherein the glycol component of the polyester comprises:
   i) 20 to 30 mole % of 2,2,4,4-tetramethyl-1,3-cyclobutanediol residues; and
   ii) 70 to 80 mole % of 1,4-cyclohexanedimethanol residues.

6. The blend of claim 1 wherein the glycol component of the polyester comprises:
   i) 30 to 40 mole % of 2,2,4,4-tetramethyl-1,3-cyclobutanediol residues; and
   ii) 60 to 70 mole % of 1,4-cyclohexanedimethanol residues.

7. The blend of claim 1 wherein the glycol component of the polyester comprises residues at least one of: ethylene glycol, diethylene glycol, 1,2-propanediol, 1,3-propanediol, neopentyl glycol, 1,4-butanediol, 1,5-pentanediol, 1,6-hexanediol, and p-xylene glycol.

8. The blend of claim 1 wherein the glycol component of the polyester comprises residues of at least one of: ethylene glycol and neopentyl glycol.

9. The blend of claim 1 wherein the glycol component of the polyester comprises ethylene glycol residues.

10. The blend of claim 1 wherein the glycol component of the polyester comprises ethylene glycol residues in the amount of 10 to 30 mole %.

11. The blend of claim 1 wherein the glycol component of polymer comprises ethylene glycol residues in the amount of 10 to 20 mole %.

12. The blend of claim 1 wherein the haze value of the blend is from 0 to 65% according to ASTM Method D1003.

13. The blend of claim 1 wherein the haze value of the blend is from 0 to 50% according to ASTM Method D1003.

14. The blend of claim 1 wherein the haze value of the blend is from 0 to 40% according to ASTM Method D1003.

15. The blend of claim 1 wherein the haze value of the blend is from 0 to 20% according to ASTM Method D1003.

16. The blend of claim 1, wherein the acid component of the polyester comprises 80 to 100 mole % of terephthalic acid residues.

17. The blend of claim 1, wherein the acid component of the polyester comprises 90 to 100 mole % of terephthalic acid residues.

18. The blend of claim 1 comprising at least one additional polymer chosen from the following nylons; polyesters other than those of claim 1; polyamides; polystyrene; polystyrene copolymers; styrene acrylonitrile copolymers; acrylonitrile butadiene styrene copolymers; poly(methylmethacrylate); acrylic copolymers; poly(ether-imides); polyphenylene oxides; poly(phenylene oxide)/polystyrene blends; polyphenylene sulfides; polyphenylene sulfide/sulfones; polysulfones; polysulfone ethers; poly(ether-ketones) of aromatic dihydroxy compounds; or mixtures thereof.

19. The blend of claim 1 wherein the polyester comprises residues of at least one branching agent.

20. The blend of claim 1 wherein the polyester comprise residues of at least one branching agent in the amount of 0.01 to 10 mole % based on the total mole percentage of the diacid or diol residues.

21. The blend of claim 1, wherein said blend has a notched Izod impact strength of at least ½ ft-lb/in at 23° C. according to ASTM D256 with a 10-mil notch in a ⅛-inch thick bar.

22. The blend of claim 1, wherein said blend has a notched Izod impact strength of at least 2 ft-lb/in at 23° C.

23. The blend of claim 1, wherein said blend has a notched Izod impact strength of at least 5 ft-lb/in at 23° C.

24. The blend of claim 1 comprising at least one additive selected from the group consisting of colorants, dyes, mold release agents, flame retardants, plasticizers, nucleating agents, UV stabilizers, glass fiber, carbon filaments, fillers, impact modifiers, or mixtures thereof.

25. The blend of claim 1 wherein the antimicrobial agent is present in the amount of 0.25 to 5 weight percent.

26. The blend of claim 1 wherein the antimicrobial agent is present in the amount of 0.01 to 3 weight percent.

27. The blend of claim 1 wherein the antimicrobial agent is a silver silica compound.

28. The blend of claim 27 wherein the antimicrobial agent is a silver magnesium silica compound.

29. The blend of claim 28 wherein the antimicrobial agent is a silver magnesium silica compound in the amount of 0.01 to 5 weight percent based on the total weight of the blend.

30. The blend of claim 1 wherein the antimicrobial agent is a silver oxide compound.

31. The blend of claim 1 wherein the antimicrobial agent is a silver glass compound.

32. An article of manufacture comprising the blend of claim 1.

33. A thermoplastic article comprising the blend of claim 1.

34. A molded article comprising the blend of claim 1.

35. A medical device comprising the blend of claim 1.

36. A medical device part comprising the blend of claim 1.

37. Packaging comprising the blend of claim 1.

38. Medical packaging comprising the blend of claim 1.

* * * * *